May 31, 1949. J. D. BROWNELL Plant Pat. 843
ROSE PLANT
Filed April 22, 1946
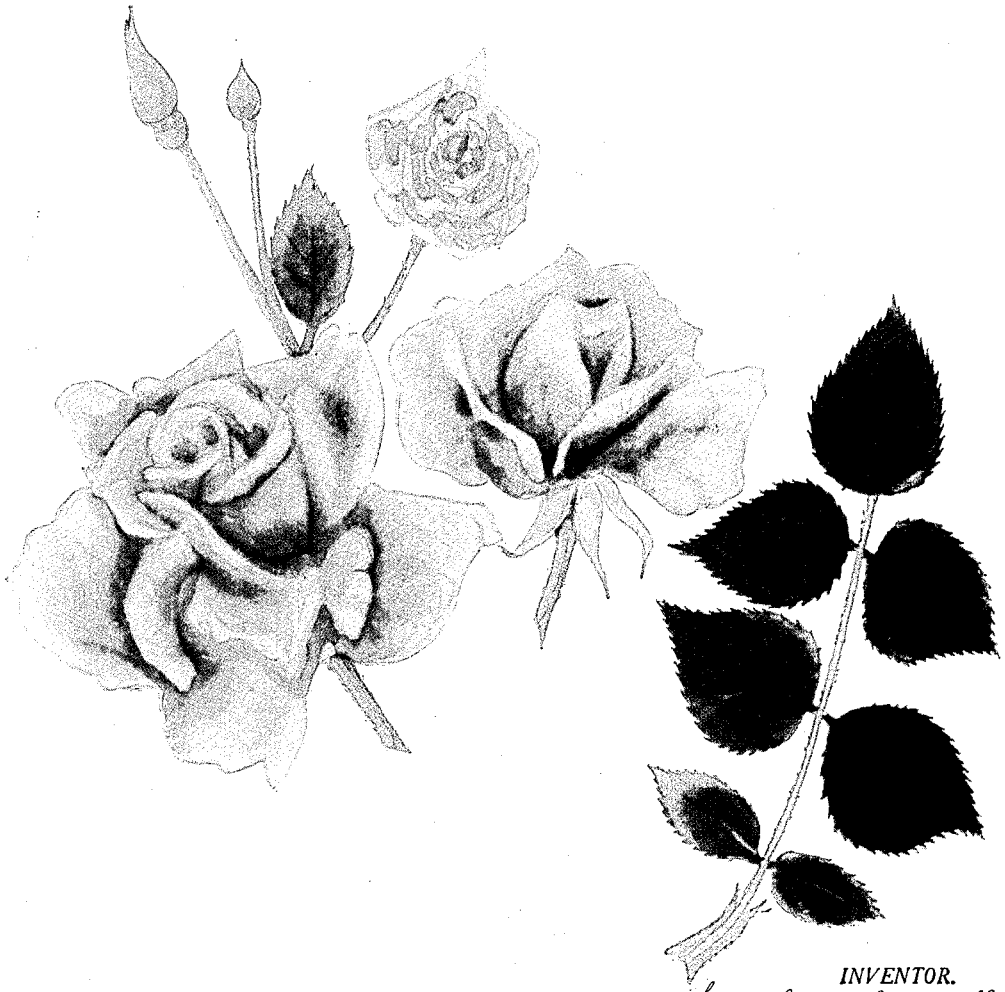
INVENTOR.
Josephine D. Brownell.
BY Patented May 31, 1949

UNITED STATES PATENT OFFICE

843

ROSE PLANT

Josephine D. Brownell, Little Compton, R. I.

Application April 22, 1946, Serial No. 663,873

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States:

The deep velvety shades (ordinary dictionary definition) of its petals, in combination with the unique brilliance thereof and their tendency to hold these colors under exposure;

The novelty and variation within certain definite limits of the form of the bloom, its character of holding that form for a long time, and the petallage of the flowers;

Its character of fragrance;

Its unusual abundance of flowers, notably after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by blackspot, under certain definite conditions of exposure, without any cultural control.

In the accompanying drawing forming a part of this specification I have shown my new rose in its natural colors, that is as near as is possible to do so artificially.

My new rose is otherwise described as follows:

*Essential information*

*Type.*—Hybrid tea, *Rosa wichuraiana* hybrid, dwarf to ascending to tall to climber, for garden display, cut flower and forcing or growing under glass.

*Class.*—Hybrid tea crossed with *Rosa wichuraiana*, further restricted by originator to include only those varieties that can survive moderately low sub-zero temperatures.

*Breeding.*—This variety was produced and bred by me and under my direction by propagation and cross pollenation.

It came into being as a seedling grown from a seed borne on a plant of Pink Princess, Plant Patent Number 459, and the pollen parent of my new rose was Crimson Glory, Plant Patent Number 105.

The pollenation that fertilized the seed that grew into my new rose, as well as the pollenation that produced one of its parents were directed by me and were performed by emasculating flowers and placing thereon a bag protecting them from self and foreign pollen. These bags were later removed and the flowers were hand pollenated with a camel's hair brush and the bags immediately replaced. The date of this pollenation was July 11, 1943.[1] The seed was planted under my direction on December 11, 1943, and the date of the first flower was July 18, 1944.

The plant and flower seemed to me to be of unusual merit and I have since made and directed extensive propagations and tests thereof.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1944–45 inclusive and the characters have successively reproduced, true to the original seedling.

*Flower*

*Habit.*—It blooms out of doors in Little Compton, beginning about three days prior to the average beginning time of commercial hybrid teas and continues relative to growth of the plant until frost.

*Flowers Borne.*—Often one and frequently two or three and occasionally more on each stem, in the usual hybrid tea type of cluster. The pedicels and peduncles are medium in diameter and length, erect, stiff, almost smooth, free from large prickles and bristles but with a few very small prickles varying to small hairs. Stems are long, medium in diameter and notably stiff and rigid.

*Quantity of Bloom.*—Free to abundant, being cumulative in quantity from year to year as the plant increases in size, notably free flowering through the summer.

*Fragrance.*—Distinctive, pleasing China tea in combination with that of *Rosa wichuraiana* under favorable environment.

*Bud.*—Neck normal as described, opens well, being little to not at all affected by hot or wet weather or both, as to color and form, except at

[1] This and other dates herein are approximate.

very high temperatures the color is less intense and the form of the petals is less recurled.

Before the calyx breaks the size is medium, form moderately pointed, occasionally with one or more sepals having foliaceous parts extending beyond the apex of the calyx up to about three quarters of an inch, the number and size of the foliaceous parts being variable and frequently having one narrow, pointed, serrate appendage on each side of the sepals, otherwise the sepals are usually normal and regular, tapering to lanceolate at their apex, turning back nearly perpendicular to the pedicel as the bud opens.

Color of the bud as the calyx opens—Ox-blood [2] to Carmine on both sides of petals.

*Bloom.*—As the bud opens and the flower develops to maturity, the color on both sides of the petals slowly changes toward Bordeaux, Spectrum Red and Rose Red. The petals have a characteristic velvety luster of unusual brilliance, more pronounced on the inner sides.

The flower is usually 4 to 5 inches in diameter when fully open, infrequently more or less, petals average around 28 to 35, frequently some smaller petals and petaloids in the center, variable in number.

The flower opens high centered, informal, recurled, showing stamens and pistils gradually. The petals are variable from obovate to ovate to irregular and frequently with surfaces variously warped and edges especially of the smaller petals frequently notably irregular. Both sides of petals have slight veining which is not prominent. The time of opening in favorable conditions is three to four days.

The petals are substantial and after about five days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Reproductive organs.*—Stamens, quantity variable, lengths medium, slightly uneven.

Anthers, Bitter Sweet Pink.

Filaments, nearly Mustard Yellow.

Pistils are several of slightly uneven length, averaging slightly over one-half inch long.

Ovaries are usually all inclosed.

Hips frequently develop to ovoid to globular, color comparable with under side of leaves with variable colored overlay on the side exposed to the sun, moderately smooth; walls, thin, fleshy.

Sepals are persistent and break off easily.

Seeds variable in number; germination to date about 10% over a variable period.

*Plant*

*Foliage.*—Is abundant, of compound leaves of three to five leaflets near the flower, five leaflets lower down the stem and frequently seven leaflets nearer the base. Size of leaflets medium, averaging in size a little larger than half way between the average hybrid tea and the *Rosa wichuraiana* leaflets. As the plants develop in size some of the leaflets develop to twice the size described above. Form of leaflets usually ovate with apex moderately acute, base rounded, margins with fine pointed serrations, petiolules short.

Color of leaflets on the upper surface is slightly variable from Dark Dull Yellow Green, with reverse side nearly Asphodel Green, edges of young leaflets slightly overlaid with Dahlia Carmine.

[2] This and color references hereinafter are to Robert Ridgway Color Standards.

The young growth more nearly compares on both sides with the color of the under sides of the leaflets, with edges and mid-ribs nearly Indian Red.

The rachises are medium, moderately narrow to slender, upper side smooth except some very short hairs on edges. Under side moderately smooth, usually 3 to 5 short prickles.

Stipules are medium in length averaging slightly under three quarters of an inch long, with points, the upper edges of which when spread in the same plane make an angle of about 95 degrees.

*Disease.*—This rose variety is moderately free from defoliation on account of black-spot and mildew.

*Growth.*—Habit, dwarf, compact, becoming bushy to tall; more cumulative in growth from year to year than the normal hybrid tea rose plant, by stems or canes from the base and by rebranching. The growth is moderately free at first, developing more rapidly after one or two years under favorable vegetative opportunity.

Color of mature stems is the same as that of the upper surface of mature leaves, shading variously lighter and also with slight overlay of Indian Red variable in intensity.

Prickles, several, usually two to four between leaves averaging in length about three eighths of an inch, shading from Dahlia Carmine to lighter at the base, turning lighter throughout and later to nearly colorless. Hairs on upper portions of stems usually same color as prickles. Tip of very young branches color of prickles rapidly changing to color of main stems.

*Winter resistance.*—A notable characteristic of this new rose is its resistance to moderate sub-zero temperatures in combination with its hybrid tea characters. This variety with grafted bud and plant entirely exposed above ground to moderate sub-zero temperatures survived and bloomed normally the following season. The word temperature herein refers to the Fahrenheit scale.

*Comparisons.*—Probably the best known roses in commerce comparable with this new variety are Nigrette (Plant Patent 87) and Red Velvet. My new variety as compared with them is in color about a combination of the two. Of petals it usually has more. In form, it is more recurled. The flower averages slightly larger and has a more sweet fragrance, it holds a deeper color longer. The plant is more cumulative in growth from year to year, can be grown into a larger plant. The foliage is smaller and more abundant, frequently with two more leaflets forming the leaves. Under exposure to black-spot this new variety is less susceptible to blackspot. It will survive after exposure to colder temperatures, to flower normally thereafter. The velvety luster is notably more intense.

I claim:

The variety of rose plant substantially as shown and described, characterized by its resistance to winter injury, its intensity and continuity of florescence, its pleasing fragrance, the color of its flower, the long keeping character of the color of its petals, their notably velvety luster and the form of its petals and the form of the flower, variable within certain definite limits, its character of long holding that form, all in association with its habit of branching from bloom stems and from the base and blooming in the hybrid tea manner and its freedom from defoliation by black-spot during the growing season.

JOSEPHINE D. BROWNELL.

No references cited.